United States Patent [19]

Abma et al.

[11] Patent Number: 5,654,464

[45] Date of Patent: Aug. 5, 1997

[54] ORGANIC PEROXIDE STABILIZATION WITH CYCLIC α-DIKETONE COMPOUNDS

[75] Inventors: Charles Abma, Marshall; Peter Frenkel; Lawrence Bock, both of Longview, all of Tex.

[73] Assignee: Witco Corporation, Greenwich, Conn.

[21] Appl. No.: 656,093

[22] Filed: May 31, 1996

[51] Int. Cl.$^6$ ............... C07C 409/32; C07C 409/34; C07C 409/36
[52] U.S. Cl. ............. 558/261; 558/264; 568/559; 568/566
[58] Field of Search ................. 558/261, 264; 568/559, 566

[56] References Cited

U.S. PATENT DOCUMENTS

| | | | |
|---|---|---|---|
| 2,415,971 | 2/1947 | Stevens | 558/261 X |
| 2,491,397 | 12/1949 | Stevens | 558/261 |
| 3,775,341 | 11/1973 | Barter | 558/261 X |
| 3,956,396 | 5/1976 | Mageli et al. | 568/559 |

*Primary Examiner*—Johann Richter
*Assistant Examiner*—Michael G. Ambrose
*Attorney, Agent, or Firm*—Scully, Scott, Murphy & Presser

[57] ABSTRACT

Organic peroxide compositions which contain a cyclic α-diketone compound to retard the rate of decomposition of the peroxide compound are disclosed.

16 Claims, No Drawings

ORGANIC PEROXIDE STABILIZATION WITH CYCLIC α-DIKETONE COMPOUNDS

BACKGROUND OF THE INVENTION

The present invention relates to organic peroxide compositions, and more specifically to peroxydicarbonate and diacyl peroxide compositions, in which a cyclic α-diketone compound has been added to retard the rate of decomposition of the peroxide compound.

Organic peroxides, such as peroxydicarbonates and diacyl peroxides, are useful as free-radical initiators in the polymerization or copolymerization of ethylenically unsaturated monomers.

For example, organic peroxides are used as initiators in the polymerization of vinyl halides, such as vinyl chloride or vinyl bromide; vinylidene halides such as vinylidene chloride; and other compounds containing polymerizable unsaturated units. The products of this well known polymerization process have extensive commercial applications.

The polymerization of vinyl halides or the copolymerization of vinyl halides with vinylidene halides is usually conducted in an aqueous medium, i.e., emulsion, solution or suspension polymerization. In such polymerizations, the monomer or mixture of monomers is dispersed in water in the presence of a surfactant and thereafter the polymerization initiated with an organic peroxide. This is a well known reaction that has been widely reported.

All organic peroxides are by their nature hazardous materials. Their usefulness depends on their ability to decompose into free radicals, shown by the following reaction:

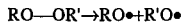

The rate of this decomposition reaction at any given temperature depends on the structure of R and R'.

The decomposition reaction is exothermic. If exothermic decomposition were to occur during production, storage, or shipment, when the peroxides are in a concentrated form, excess pressure development and/or fire or explosion could result. Consequently, many organic peroxides must be kept refrigerated.

There have been several reports in recent years of the retardation of the rate of decomposition of organic peroxides.

The Journal of The American Chemical Society, Volume 72, pages 1254 to 1263 (1950), discloses the use of, for example, ethyl acetoacetate, iodine, trinitrobenzene, acetanilide, nitromethane, phenol, hydrogen peroxide and tetralin to retard the rate of decomposition of diisopropyl peroxydicarbonate.

U.S. Pat. No. 4,515,929 (1985) reports aqueous dispersions of organic peroxides including peroxydicarbonates, which are stabilized against decomposition by the addition of diphenyl peroxydicarbonate or di(alkyl substituted) phenyl peroxydicarbonates.

U.S. Pat. No. 4,552,682 (1985) discloses the use of phenolic antioxidants to retard the rate of degradation of aqueous organic peroxide dispersions. The use of phenolic antioxidants is undesirable because they result in discoloration.

U.S. Pat. No. 5,155,192 (1992) discloses the use of organic hydroperoxides, e.g., tert-butyl hydroperoxide, to retard the rate of decomposition of peroxydicarbonates.

Research Disclosure, April, 1995, page 275, reports the thermal stabilization of dialkyl peroxydicarbonates using unsaturated nitriles or unsaturated acetylenic compounds.

SUMMARY OF THE INVENTION

The present invention relates to the use of certain non-peroxide compounds which are effective in retarding the decomposition of organic peroxides such as peroxydicarbonates and diacyl peroxides. Thus, one aspect of the present invention is a composition containing an organic peroxide compound selected from the group consisting of peroxydicarbonate and diacyl peroxide compounds and at least one cyclic α-diketone compound which reduces the rate of decomposition of the peroxide. Another aspect of the present invention is the method of stabilizing a peroxydicarbonate or diacyl peroxide against decomposition, comprising adding thereto a cyclic α-diketone compound in an amount effective to achieve said stabilization.

In particular, cyclic α-diketone compounds useful in the present invention include those of Formula (I):

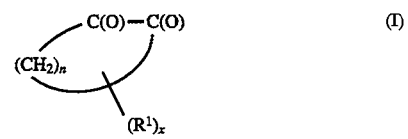

wherein n is 1–6, x is 0–2n, and $R^1$ is alkyl containing 1 to 22 carbon atoms, phenyl, or phenyl substituted with one or more of alkyl containing 1 to 22 carbon atoms, halogen, and hydroxy, and when x is greater than 1, each occurrence of $R^1$ can be the same or different and can be on the same or different ring carbon atoms.

DETAILED DESCRIPTION OF THE INVENTION

The present invention relates to compositions containing an organic peroxide, which is a peroxydicarbonate or a diacyl peroxide, and at least one cyclic α-diketone stabilizing compound to retard the rate of decomposition of the peroxide compound.

Cyclic α-diketone compounds useful in the present invention are of the following general Formula (I):

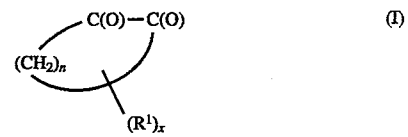

In Formula (I), n is 1–6 and preferably 3–5; x is zero up to 2n; and $R^1$ is phenyl, alkyl containing 1 to 22 carbon atoms and preferably 1 to 5 carbon atoms, or substituted phenyl. The phrase "substituted phenyl" refers to phenyl substituted with alkyl containing 1 to 22 carbon atoms, halogen (i.e. fluorine, chlorine, bromine, and/or iodine), and/or hydroxy, or with any two or more of any such groups. That is, when two or more of such substituents are present they can be the same or different.

In all cases, alkyl substituents can be straight-chain; branched; cycloalkyl or cycloalkylalkyl. The cycloalkyl structure in the latter two cases may optionally be alkyl substituted.

Preferred embodiments useful in the present invention include compounds of Formula (I) such as 3-methyl-1, 2-cyclopentanedione (wherein n is 3, x is 1, and $R^1$ is 3-methyl); 3-ethyl-1,2-cyclopentanedione (wherein n is 3, x is 1, and $R^1$ is 3-ethyl); 1,2-cyclohexanedione (wherein n is 4 and x is zero) and 1,2-cyclopentanedione (wherein n is 3 and x is zero).

Cyclic α-diketone compounds of Formula (I) are commercially available and/or can be synthesized from commercially available starting materials by use of procedures familiar to one of ordinary skill in the art.

The amount of cyclic α-diketone to use in the compositions and methods of the present invention is an amount sufficient to retard the rate of decomposition of the peroxide compound. The preferred amount of cyclic α-diketone is a concentration of 0.2–5.0% by weight of the peroxydicarbonate or diacyl peroxide present. The exact amount will vary and depend on both the peroxide compound and the cyclic α-diketone used, and on the conditions to which the peroxide composition is exposed.

The cyclic α-diketone can if desired be used in solution in an appropriate solvent. Suitable solvents for the cyclic α-diketone can be chosen from among alcohols, glycols and esters; an example is propylene glycol.

Peroxide compounds with which this invention is particularly useful are of the general structural formula II:

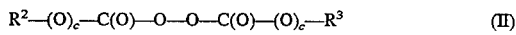

$$R^2-(O)_c-C(O)-O-O-C(O)-(O)_c-R^3 \quad\quad (II)$$

where each c is 0 or 1, and $R^2$ and $R^3$ can each be an aliphatic, cycloaliphatic or aromatic group with 1 to 22 carbon atoms, preferably 2 to 8 carbon atoms. When the subscripts c are zero, the compound is a diacyl peroxide, and when the subscripts c are one, the compound is a peroxydicarbonate. $R^2$ and $R^3$ may be branched or non-branched, substituted or unsubstituted alkyl, alkenyl, cycloalkyl or aromatic groups.

Examples of $R^2$ and $R^3$ groups include phenyl, methyl, ethyl, n-propyl, isopropyl, n-butyl, sec-butyl, t-butyl, isobutyl, hexyl, octyl, neopentyl, 2-ethylhexyl, capryl, lauryl, myristyl, cetyl, stearyl, allyl, methallyl, crotyl, cyclohexyl, 4-t-butylcyclohexyl, 4-t-amylcyclohexyl, benzyl, 2-phenylethyl, 2-phenylbutyl, α-carbethoxyethyl, β-methoxyethyl, 2-phenoxyethyl, 2-methoxyphenyl, 3-methoxyphenyl, 2-ethoxyethyl, 2-ethoxyphenyl, 3-methoxybutyl, 2-carbamyloxyethyl, 2-chloroethyl, 2-nitrobutyl and 2-nitro-2-methylpropyl.

Specific examples of peroxydicarbonates include diethyl peroxydicarbonate, di-n-butyl peroxydicarbonate, diisobutyl peroxydicarbonate, and di-4-tert-butylcyclohexyl peroxydicarbonate. Preferably the peroxydicarbonate is di-sec-butyl peroxydicarbonate, di-2-ethylhexyl peroxydicarbonate, di-n-propyl peroxydicarbonate or diisopropyl peroxydicarbonate.

Specific examples of diacyl peroxides include benzoyl peroxide, dilauroyl peroxide, didecanoyl peroxide, diacetyl peroxide, and di(3,5,5-trimethylhexanoyl) peroxide.

The peroxide compound may be symmetrical or unsymmetrical i.e., $R^2$ and $R^3$ may be the same or different. The peroxide may be a homogeneous mixture containing symmetric peroxides, asymmetric peroxides such as isopropyl-sec-butyl peroxydicarbonate or 2-methylpropionyl-3-methylpentanoyl peroxide or a mixture of symmetric and asymmetric peroxides such as mixtures of diisopropyl peroxydicarbonate, di-sec-butyl peroxydicarbonate and isopropyl-sec-butyl peroxydicarbonate as disclosed in U.S. Pat. No. 4,269,726.

The peroxydicarbonate compounds and diacyl peroxide compounds can be synthesized by conventional techniques familiar to one of ordinary skill in the art. Peroxydicarbonates are typically prepared by reacting the corresponding alkyl chloroformate with aqueous sodium peroxide at low temperatures, 0°–20° C. See U.S. Pat. No. 2,370,588 and the Journal of the American Chemical Society, Volume 72, page 1254 (1950). Diacyl peroxides are typically made from acid chlorides using synthetic techniques familiar to one of ordinary skill in the art.

Preferably, the peroxydicarbonates and diacyl peroxides with which this invention is useful include those which are a liquid at 0° C. and more preferably a liquid at –5° C. Still more preferred are the peroxydicarbonates and diacyl peroxides which are liquid down to –20° C.

The present invention is especially applicable to aqueous dispersions of peroxydicarbonates and diacyl peroxides that are useful as initiators in the free radical polymerization of ethylenically unsaturated materials, particularly in an aqueous medium, e.g., suspension or emulsion polymerization. A dispersion of the peroxide is prepared by dispersing it in water with a suitable dispersing aid, e.g., a surfactant or emulsifying agent. Surfactants and emulsifying agents useful in the formulations of such dispersions are well known in this field and are quite numerous.

To prepare dispersions in accordance with the present invention, the cyclic α-diketone compound or its solution may be added to an already-formed peroxide dispersion, or to the water containing the surfactant, or to the peroxide before the dispersion is formed. Dispersions of the present invention generally contain 20 to 70% by weight, preferably 30 to 60% by weight, of the peroxydicarbonate compound or diacyl peroxide and 0.2 to 5% (by weight of the peroxide) of the cyclic α-diketone.

The manner of preparation of peroxide dispersions is known to one of ordinary skill in the art. A description of peroxydicarbonate dispersions and their preparation can be found in U.S. Pat. No. 4,515,929; U.S. Pat. No. 3,825,509; U.S. Pat. No. 3,988,261 and U.S. Pat. No. 4,092,470.

Peroxide compositions of the present invention may also be prepared as physical mixtures in the form of liquids, granules, powders or flakes. A physical mixture in accordance with the present invention may be prepared by mixing a liquid peroxide compound or a solution of a peroxide in a suitable solvent with the desired amount of cyclic α-diketone in a conventional mixing apparatus. The resulting mixture is then, if desired, granulated, pulverized or flaked. The cyclic α-diketone may be added either (1) to the chloroformate- or acid chloride-containing reaction mixture before preparation of the peroxide compound or (2) to the unprocessed reaction mixture immediately after the preparation of the peroxide compound. Either (1) or (2) will ensure that the two components are mixed as homogeneously as possible in order to receive the greatest possible benefit from the stabilizing effect of the cyclic α-diketone.

A solution of the present invention may be prepared by combining the desired amounts of cyclic α-diketone compound or its solution and peroxide in a suitable solvent.

Suitable organic solvents include those normally employed for peroxydicarbonate or diacyl peroxides, such as esters of phthalic acid, an example of which is dibutyl phthalate, and aliphatic and aromatic hydrocarbons and mixtures of such hydrocarbons, examples of which are hexane, odorless mineral spirits, mineral oil, benzene, toluene, xylene and (iso)paraffins such as isododecane. Other suitable solvents will be familiar to one of ordinary skill in the art.

Solutions according to the present invention contain at least 10% by weight and preferably at least 25% by weight of a peroxydicarbonate or diacyl peroxide compound.

The peroxide compositions of the present invention display numerous significant advantages. Chief among these is improved thermal stability, both in response to exposure to elevating temperature and in response to exposure to a given constant temperature. Thermal stability of self-reactive substances, in response to elevating temperatures, can be determined by measuring the self accelerating decomposition temperature (SADT). SADT is one of the recognized characteristics for determining the safe storage and transportation of materials such as organic peroxides. [Recommendations on the Transport of Dangerous Goods, 9th ed, United Nations, N.Y. 1995, Section 11.3.5, page 264].

SADT can be directly correlated with the onset temperature as measured in a differential thermal analyzer (DTA). The onset temperature is the point at which an uncontrolled thermal decomposition starts. The onset temperature can be measured by determining the point at which the rate of temperature increase in a sealed cell exceeds a certain pre-determined value. In addition, the onset temperature can be measured by determining the point at which the rate of pressure increase in the sealed cell exceeds a certain pre-determined value.

Thermal stability in response to a given constant temperature can be assessed by means of accelerated aging tests at, for instance, 15° C.

The cyclic α-diketone compounds of the present invention increase the onset temperature of both peroxydicarbonates and diacyl peroxides.

Also, the cyclic α-diketone compounds do not detract from the effectiveness of the peroxide as a polymerization initiator.

The following examples are intended to illustrate the claimed invention and are not in any way designed to limit its scope. Numerous additional embodiments within the scope and spirit of the claimed invention will become apparent to those skilled in the art.

EXAMPLE 1

The onset temperature was measured and compared for samples of pure di-2-ethylhexyl peroxydicarbonate and samples of di-2-ethylhexyl peroxydicarbonate in the presence of each of several different cyclic α-diketone compounds. The liquid mixtures were prepared by dissolving into the peroxydicarbonate a sufficient amount of a solution of the α-diketone in propylene glycol to provide the indicated amount of the α-diketone.

Using a type of Differential Thermal Analyzer (Radex Solo Thermal Analyzer, marketed by Astra Scientific International, Pleasanton, Calif.), with an isothermal hold temperature of 30° C. for 15 minutes and then a temperature increase of 1°/minute to 130° C., the onset temperature was measured for a one gram sample of di-2-ethylhexyl peroxydicarbonate in a sealed cell.

The onset temperature was measured both by noting the point where the rate of increase (ΔT) of the sample temperature reached 0.2° C./minute and also the point where the rate of increase in pressure (ΔP) of the closed sample cell reached 1.0 psi/minute. ΔT is the difference between the oven temperature and the sample temperature. ΔP is the difference between a reference pre-calibrated pressure and the pressure developed in the sealed sample cell.

The procedure was repeated with separate samples of the above peroxydicarbonate containing, in turn, solutions (in propylene glycol) of 3-methyl-1,2-cyclopentanedione (MCPD), 3-ethyl-1,2 cyclopentanedione (ECPD) and 1,2-cyclohexanedione (CHD). The results are shown in Table I. Results obtained with ethyl acetoacetate, which is disclosed in the prior art, are included for comparison.

The results show that the presence of a compound in accordance with the present invention increases the temperature at which self accelerating decomposition of the peroxydicarbonate will begin. This shows that the cyclic α-diketone compound is an effective stabilizer and is superior to ethyl acetocetate. The results also show that the effect is concentration dependent, with the decomposition beginning at a higher temperature when more cyclic α-diketone compound is present.

TABLE I

ONSET TEMPERATURE FOR PURE DI-2-ETHYLHEXYL PEROXYDICARBONATE

| Sample Purity, % | Additive | Wt. % of Pure Additive Used | Onset Temperature (°C.) by ΔT | Onset Temperature (°C.) by ΔP |
|---|---|---|---|---|
| 97.7 | None | — | 36.3 | 42.3 |
|  | ECPD-50** | 1.8 | 54.8 | 57.2 |
| 97.4% | None |  | 34.4 | 38.8 |
|  | Ethylaceto-acetate | 3.0 | 43.4 | 46.3 |
|  | MCPD-10* | 0.3 | 42.8 | 45.7 |
|  | MCPD-10 | 0.5 | 48.4 | 50.1 |
|  | CHD-60*** | 0.6 | 42.3 | 44.9 |
|  | CHD-60 | 1.8 | 48.4 | 49.0 |
|  | CHD-60 | 3.0 | 51.3 | 52.1 |

*MCPD-10 = 10% solution of MCPD in propylene glycol
**ECPD-50 = 50% solution of ECPD in propylene glycol
***CHD-60 = 60% solution of CHD in propylene glycol

EXAMPLE 2

The onset temperatures for samples of di-2-ethylhexyl peroxydicarbonate diluted with odorless mineral spirits (OMS) and samples of di-2-ethylhexyl peroxydicarbonate diluted in OMS in the presence of several different cyclic α-diketone compounds were measured and compared.

The liquid mixtures were prepared by dissolving into the peroxydicarbonate solution a sufficient amount of a solution of ECPD, MCPD or CHD in propylene glycol, to provide the indicated amount of the cyclic α-diketone compound.

Using the same apparatus and procedure as described in Example 1, the onset temperature for a one gram sample of di-2-ethylhexyl peroxydicarbonate diluted in OMS was measured. The procedure was repeated with separate samples of the above solution to which a solution of cyclic α-diketone had been added. The results are shown in Table II. Results obtained with ethyl acetoacetate, which is disclosed in the prior art, are included for comparison.

As can be seen in Table II, the addition of a cyclic α-diketone compound in accordance with the present invention increases the temperature at which self accelerating decomposition of the peroxydicarbonate solution will begin. The results also show that the effect is concentration dependent, with the decomposition beginning at a higher temperature when more cyclic α-diketone compound is present.

TABLE II

ONSET TEMPERATURE FOR DI-2-ETHYLHEXYL PEROXYDICARBONATE IN OMS

| Sample Purity, % | Additive | Wt. % of Pure Additive Used | Onset Temperature (°C.) by $\Delta T$ | by $\Delta P$ |
|---|---|---|---|---|
| 74.9 | None | — | 41.4 | 43.6 |
| | ECPD-50* | 0.2 | 44.9 | 46.3 |
| | ECPD-50 | 0.4 | 48.5 | 48.5 |
| | ECPD-50 | 0.5 | 50.2 | 52.1 |
| | ECPD-50 | 0.9 | 54.1 | 54.8 |
| | ECPD-50 | 1.5 | 56.2 | 57.4 |
| | ECPD-50 | 2.5 | 57.0 | 58.9 |
| 75.1 | None | | 40.7 | 45.0 |
| | Ethylaceto-acetate | 3.0 | 44.5 | 45.9 |
| | MCPD-10** | 0.1 | 41.6 | 45.3 |
| | MCPD-10 | 0.3 | 47.0 | 49.3 |
| | MCPD-10 | 0.5 | 48.6 | 50.4 |
| | CHD-60*** | 0.6 | 46.9 | 49.0 |
| | CHD-60 | 1.2 | 50.9 | 52.5 |
| | CHD-60 | 1.9 | 53.0 | 53.9 |

*ECPD-50 = 50% solution of ECPD in propylene glycol
**MCPD-10 = 10% solution of MCPD in propylene glycol
***CHD-60 = 60% solution of CHD in propylene glycol

EXAMPLE 3

The onset temperatures for samples of di-sec-butyl peroxydicarbonate diluted in odorless mineral spirits (OMS) and samples of di-sec-butyl peroxydicarbonate diluted in OMS in the presence of several different cyclic α-diketone compounds were measured and compared. The liquid mixtures were prepared by dissolving into the peroxydicarbonate solution a sufficient amount of a solution of ECPD, MCPD or CHD in propylene glycol to provide the indicated amount of α-diketone compound. The onset temperature was measured according to the procedure described in Example I.

As can be seen in Table III, the presence of a cyclic α-diketone compound in accordance with the present invention increases the temperature at which self accelerating decomposition of the peroxydicarbonate solution will begin. The results also show that the effect is concentration dependent, with the reaction beginning at a higher temperature when more cyclic α-diketone compound is present. The effect of ethyl acetoacetate is included for comparison.

TABLE III

ONSET TEMPERATURE FOR DI-SEC-BUTYL PEROXYDICARBONATE IN OMS

| Sample Purity, % | Additive | Wt. % of Pure Additive Used | Onset Temperature (°C.) by $\Delta T$ | by $\Delta P$ |
|---|---|---|---|---|
| 76.2 | None | — | 36.6 | 41.0 |
| | ECPD-50* | 1.5 | 52.5 | 53.0 |
| 70.7 | None | | 37.0 | 37.9 |
| | Ethylaceto-acetate | 3.0 | 36.3 | 39.3 |
| | MCPD-10** | 0.1 | 39.9 | 41.3 |
| | MCPD-10 | 0.3 | 44.2 | 46.7 |
| | MCPD-10 | 0.5 | 46.8 | 48.1 |
| | CHD-60*** | 0.6 | 43.6 | 45.0 |

TABLE III-continued

ONSET TEMPERATURE FOR DI-SEC-BUTYL PEROXYDICARBONATE IN OMS

| Sample Purity, % | Additive | Wt. % of Pure Additive Used | Onset Temperature (°C.) by $\Delta T$ | by $\Delta P$ |
|---|---|---|---|---|
| | CHD-60 | 1.8 | 50.0 | 50.7 |
| | CHD-60 | 3.0 | 52.8 | 53.8 |

*ECPD-50 = 50% solution of ECPD in propylene glycol
**MCPD-10 = 10% solution of MCPD in propylene glycol
***CHD-60 = 60% solution of CHD in propylene glycol

EXAMPLE 4

The effect of the presence of ECPD on the storage stability at 15° C. of pure di-2-ethylhexyl peroxydicarbonate, di-2-ethylhexyl peroxydicarbonate dissolved in odorless mineral spirits (OMS), and di-sec-butyl peroxydicarbonate dissolved in OMS was determined as an accelerated aging test. The results are presented in Table IV.

The purity of the peroxydicarbonate was measured at the times indicated in Table IV. The initial purity values in the Table were corrected for the presence of the additive.

The results show that the presence of a cyclic α-diketone, in accordance with the present invention, retards the rate of decomposition of the peroxydicarbonate.

TABLE IV

Purity vs. Time at 15° C. for Several Peroxydicarbonates (ECPD was added as a 50% solution in propylene glycol)

| Peroxydicarbonate | Additive | Wt. % of Pure Additive Used | Purity (%) Start | 7 Days | 14 Days | 21 Days |
|---|---|---|---|---|---|---|
| 97.7% Di-2-ethylhexyl Peroxydicarbonate (pure) | none | — | 97.7 | 37.3 | 22.4 | 21.7 |
| 97.7% Di-2-ethylhexyl Peroxydicarbonate (pure) | ECPD-50 | 1.5 | 94.9 | 77.3 | 39.3 | 27.1 |
| 74.9% Di-2-ethylhexyl Peroxydicarbonate in OMS | none | — | 74.9 | 28.6 | 17.9 | 15.4 |
| 74.9% Di-2-ethylhexyl Peroxydicarbonate in OMS | ECPD-50 | 1.5 | 72.7 | 58.8 | 37.7 | 23.1 |
| 76.2% Di-sec-butyl Peroxydicarbonate in OMS | none | — | 76.2 | 19.9 | 17.7 | — |
| 76.2% Di-sec-butyl Peroxydicarbonate in OMS | ECPD-50 | 1.4 | 74.2 | 49.5 | 20.7 | — |

EXAMPLE 5

The onset temperatures for a sample of pure di-(3,5,5-trimethylhexanoyl) peroxide and samples of pure di-(3,5,5-trimethylhexanoyl) peroxide in the presence of two different cyclic α-diketones were measured and compared. This procedure was repeated for a sample of di-(3,5,5-trimethylhexanoyl) peroxide dissolved in odorless mineral spirits (OMS) and samples of di-(3,5,5-trimethylhexanoyl) peroxide dissolved in OMS in the presence of two different cyclic α-diketone compounds.

The liquid mixtures were prepared by adding a sufficient amount of a solution of ECPD or CHD in propylene glycol to the diacyl peroxide to provide the indicated amount of the cyclic α-diketone compound. The procedure described in Example 1 was followed. The results are shown in Table V.

As can be seen in Table V, the presence of the cyclic α-diketone compound, in accordance with the present invention, increases the temperature at which self accelerating decomposition of the diacyl peroxide, or its solution in OMS, will begin.

TABLE V

ONSET TEMPERATURE FOR
DI(3,5,5-TRIMETHYLHEXANOYL) PEROXIDE

| Sample Purity, % | Additive | Wt. % of pure Additive Used | Onset Temperature (°C.) by ΔT | by ΔP |
|---|---|---|---|---|
| 98.2 | None | | 68.2 | 67.7 |
| | CHD-60* | 3.0 | 70.1 | 72.3 |
| | ECPD-50** | 2.6 | 70.8 | 74.4 |
| 60.1 (in OMS) | None | | 74.9 | 76.1 |
| | CHD-60* | 2.0 | 76.6 | 76.6 |
| | ECPD-50** | 1.5 | 77.0 | 77.0 |

*CHD-60 = 60% solution of CHD in propylene glycol
**ECPD-50 = 50% solution of ECPD in propylene glycol

We claim:

1. A composition comprising:

a. an organic peroxide component selected from the group consisting of peroxydicarbonate compounds, diacyl peroxides, and mixtures thereof; and b. a sufficient amount of a stabilizer to retard the rate of decomposition of the organic peroxide component, wherein said stabilizer is selected from the group consisting of compounds of Formula (I):

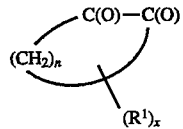

(I)

and mixtures thereof, wherein n ms 1–6, x is 0–2n, and

R$^1$ is alkyl containing 1 to 22 carbon atoms, phenyl, or phenyl substituted with one or more of alkyl containing 1 to 22 carbon atoms, halogen, and hydroxy, and when x is greater than 1, each occurrence of R$^1$ can be the same or different and can be on the same or different ring carbon atoms.

2. A composition according to claim 1 wherein said organic peroxide component comprises at least one compound of the Formula (II)

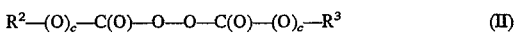

wherein R$^2$ and R$^3$ are independently aliphatic, cycloaliphatic or aromatic groups containing 1 to 22 carbon atoms, and c is zero or one.

3. A composition according to claim 2 wherein in Formula (II) both subscripts c are one.

4. A composition according to claim 2 wherein in Formula (II) both subscripts c are zero.

5. A composition according to claim 2 wherein R$^2$ and R$^3$ are independently selected from the group consisting of phenyl, methyl, ethyl, n-propyl, isopropyl, n-butyl, sec-butyl, t-butyl, isobutyl, hexyl, octyl, neopentyl, 2-ethylhexyl, capryl, lauryl, myristyl, cetyl, stearyl, allyl, methallyl, crotyl, cyclohexyl, 4-t-butylcyclohexyl, 4-t-amylcyclohexyl, benzyl, 2-phenylethyl, 2-phenylbutyl, α-carbethoxyethyl, β-methoxyethyl, 2-phenoxyethyl, 2-methoxyphenyl, 3-methoxyphenyl, 2-ethoxyethyl, 2-ethoxyphenyl, 3-methoxybutyl, 2-carbamyloxyethyl, 2-chloroethyl, 2-nitrobutyl and 2-nitro-2-methylpropyl.

6. A composition according to claim 1 wherein said stabilizer is selected from the group consisting of 3-methyl-1,2-cyclopentanedione, 3-ethyl-1,2-cyclopentanedione, 1,2-cyclohexanedione, 1,2-cyclopentanedione, and mixtures thereof.

7. A composition according to claim 1 wherein said stabilizer comprises 0.2 to 5% by weight of said organic peroxide component.

8. A composition according to claim 1 wherein said organic peroxide component is selected from the group consisting of di-2-ethylhexyl peroxydicarbonate, di-sec-butylperoxydicarbonate, diethyl peroxydicarbonate, di-n-butyl peroxydicarbonate, isopropyl-sec-butyl peroxydicarbonate, di-4-tert-butylcyclohexyl peroxydicarbonate, di-n-propyl peroxydicarbonate, diisopropyl peroxydicarbonate, benzoyl peroxide, dilauroyl peroxide, didecanoyl peroxide, diacetyl peroxide, 2-methylpropionyl-3-methylpentanoyl peroxide, and di-(3,5,5-trimethylhexanoyl) peroxide and mixtures thereof.

9. The method of retarding the rate of decomposition of an organic peroxide selected from the group consisting of peroxydicarbonate and diacyl peroxide compounds and mixtures thereof comprising adding to said organic peroxide a stabilizer in amount thereof effective to inhibit said decomposition, wherein said stabilizer is selected from the group consisting of compounds of Formula (I):

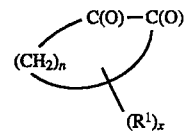

(I)

and mixtures thereof, wherein n is 1–6, x is 0–2n, and

R$^1$ is alkyl containing 1 to 22 carbon atoms, phenyl, or phenyl substituted with one or more of alkyl containing 1 to 22 carbon atoms, halogen, and hydroxy, and when x is greater than 1, each occurrence of R$^1$ can be the same or different and can be on the same or different ring carbon atoms.

10. A method according to claim 9 wherein said peroxydicarbonate and diacyl peroxide compounds correspond to Formula (II):

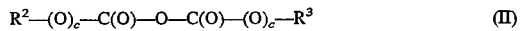

(II)

wherein $R^2$ and $R^3$ are independently aliphatic, cycloaliphatic or aromatic groups containing 1 to 22 carbon atoms, and c is zero or one.

11. A method according to claim 10 wherein in Formula (II) both subscripts c are one.

12. A method according to claim 10 wherein in Formula (II) both subscripts c are zero.

13. A method according to claim 10 wherein $R^2$ and $R^3$ are independently selected from the group consisting of phenyl, methyl, ethyl, n-propyl, isopropyl, n-butyl, sec-butyl, t-butyl, isobutyl, hexyl, octyl, neopentyl, 2-ethylhexyl, capryl, lauryl, myristyl, cetyl, stearyl, allyl, methallyl, crotyl, cyclohexyl, 4-t-butylcyclohexyl, 4-t-amylcyclohexyl, benzyl, 2-phenylethyl, 2-phenylbutyl, α-carbethoxyethyl, β-methoxyethyl, 2-phenoxyethyl, 2-methoxyphenyl, 3-methoxyphenyl, 2-ethoxyethyl, 2-ethoxyphenyl, 3-methoxybutyl, 2-carbamyloxyethyl, 2-chloroethyl, 2-nitrobutyl and 2-nitro-2-methylpropyl.

14. A method according to claim 9 wherein said stabilizer is selected from the group consisting of 3-methyl-1,2-cyclopentanedione, 3-ethyl-1,2-cyclopentanedione, 1,2-cyclohexanedione, 1,2-cyclopentanedione and mixtures thereof.

15. A method according to claim 9 wherein the amount of said stabilizer is 0.2 to 5% by weight of said organic peroxide.

16. A method according to claim 9 wherein said organic peroxide component is selected from the group consisting of di-2-ethylhexyl peroxydicarbonate, di-sec-butylperoxydicarbonate, diethyl peroxydicarbonate, di-n-butyl peroxydicarbonate, isopropyl-sec-butyl peroxydicarbonate, di-4-tert-butylcyclohexyl peroxydicarbonate, di-n-propyl peroxydicarbonate, diisopropyl peroxydicarbonate, benzoyl peroxide, dilauroyl peroxide, didecanoyl peroxide, diacetyl peroxide, 2-methylpropionyl-3-methylpentanoyl peroxide, and di-(3,5,5-trimethylhexanoyl) peroxide and mixtures thereof.

* * * * *